United States Patent [19]

Castaneda

[11] 4,210,133
[45] Jul. 1, 1980

[54] VAGINAL MICROSCOPE

[75] Inventor: Jimeno O. Castaneda, Colonia Lindavista, Mexico

[73] Assignee: Consejo Nacional de Ciencia y Tecnologia, Mexico, Mexico

[21] Appl. No.: 734,098

[22] Filed: Oct. 20, 1976

[30] Foreign Application Priority Data

Oct. 21, 1975 [MX] Mexico .................................. 89285

[51] Int. Cl.² .......................... A61B 1/00; A61B 1/06; A61B 1/30
[52] U.S. Cl. .......................................... 128/6; 128/3
[58] Field of Search .................... 128/11, 4–9, 128/13, 17, 18, 20, 23, 3; 350/38, 91, 19, 235–238; 240/2 MA; 354/79, 76, 75

[56] References Cited

U.S. PATENT DOCUMENTS

| 872,343 | 12/1907 | Griswold | 128/18 |
|---|---|---|---|
| 1,311,186 | 6/1919 | Silverman | 240/2 MA |
| 1,444,400 | 2/1923 | Silverman | 350/235 |
| 1,521,339 | 12/1924 | Taylor | 350/38 |
| 1,896,861 | 2/1933 | Cameron | 128/9 |
| 2,691,918 | 10/1954 | Robins et al. | 240/2 MA |
| 2,697,431 | 12/1954 | Antoine et al. | 128/6 |
| 2,705,490 | 4/1955 | Littman | 350/236 |
| 3,005,452 | 10/1961 | Pitman | 128/11 |
| 3,146,775 | 9/1964 | Moore | 128/6 |
| 3,744,481 | 7/1973 | McDonald | 128/12 |
| 3,789,829 | 2/1974 | Hasson | 128/17 |

FOREIGN PATENT DOCUMENTS

| 78668 | 3/1919 | Austria | 128/3 |
|---|---|---|---|
| 571599 | 3/1933 | Fed. Rep. of Germany | 128/4 |
| 703073 | 1/1944 | Fed. Rep. of Germany | 128/4 |
| 703073 | 1/1954 | United Kingdom | 128/4 |
| 1322044 | 7/1973 | United Kingdom | 128/4 |

Primary Examiner—V. Millin
Attorney, Agent, or Firm—Finnegan, Henderson, Farabow, Garrett & Dunner

[57] ABSTRACT

An improved instrument for microscopic examination through the throat of the womb including a guide-tube and a microscope. The guide-tube is adjustably attached to a vaginal speculum and has its own illumination system, a graduated collar for focusing the microscope, and fine-adjustment clamps for preventing the accidental movements of the microscope. The microscope is adjustably positioned in the guide-tube so that it can focus on a plurality of microscopic fields without movement of the guide-tube. It has two illumination systems, one providing light for vision, the other an electronic flash for a photographic camera. The microscope can be removed from the stationary guide-tube, its objectives and oculars replaced by elements with different powers, and reinserted in the guide-tube to provide examination at variable magnifications.

15 Claims, 7 Drawing Figures

VAGINAL MICROSCOPE

FIELD OF THE INVENTION

This invention relates to an instrument for examination of the tissues of the throat of the womb with microscopic accuracy utilizing variable magnifying powers at will by use of interchangeable objectives and oculars. This invention is highly useful and accurate in the diagnosis of cancer of the cervical uterus.

SUMMARY OF THE INVENTION

The vaginal microscope of the invention has many advantages, of which the main ones are listed below:

(1) It permits examination of previously stained tissues with microscopic definition at their original site in the body thereby avoiding the changes undergone by excised cells (as is the case in the Papanicolaou test) and avoiding shearing of tissue fragments (as in biopsy), in a method which is painless and allows examination as often as is deemed necessary.

(2) The instrument may be coupled to any photographic camera equipped with suitable accessories for microscopes and permits pictures to be taken in black-and-white and in color, thus facilitating an accurate monitoring of the changes and modifications undergone by the tissues with the passage of time.

(3) The instrument is small and light and may be directly fastened to a vaginal speculum, thereby providing easy handling. Furthermore, it is economical.

(4) The system comprises three independent illumination systems, two of which use arbitrarily variable light intensity, the third of which flashes electronically. The first two permit emplacement of the instrument with perfect visual monitoring and observation of the pertinent tissues at selected magnification. The third permits instantaneous photographs to be taken.

(5) The instrument includes two parts: a guide-tube with its own illumination, and the actual microscope with its corresponding illumination systems.

The guide-tube is fastened to the vaginal speculum already emplaced in the woman's vagina, and the microscope is coupled to the guide-tube which is placed in position so as to permit examination of the desired tissue portion.

(6) By means of the mechanism to be described below, once the guide-tube and the microscope are in place, and without changing the position of the former, numerous microscopic fields may be examined at any effective magnification from 25 to 900.

Additional objects and advantages of the invention will be set forth in part in the description which follows, and in part will be obvious from the description, or may be learned by the practice of the invention. The objects and advantages of the invention may be realized and attained by means of the instrumentalities and combinations particularly pointed out in the appended claims.

The accompanying drawings, which are incorporated in and constitute a part of this specification, illustrate one embodiment of the invention and together with the description, serve to explain the principles of the invention.

DESCRIPTION OF THE PREFERRED EMBODIMENT

Reference will now be made in detail to the present preferred embodiment of the invention, an example of which is illustrated in the accompanying drawings.

Figure 1:
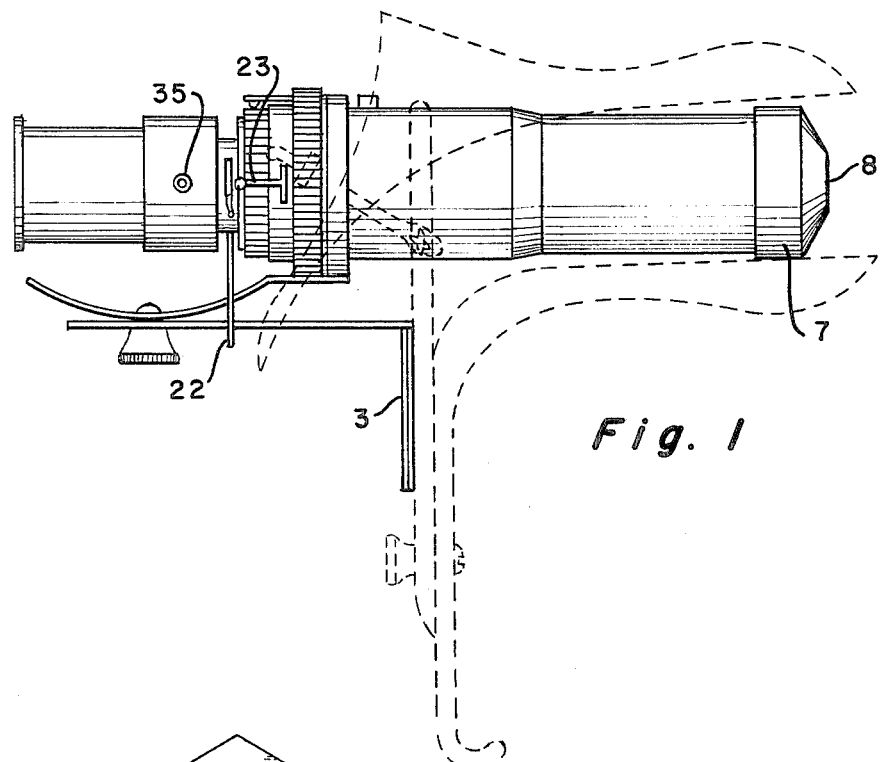
FIG. 1 is a side view of an assembled vaginal microscope constructed in accordance with the teachings of this invention.

The preferred embodiment of the instrument of the invention is shown in FIG. 1. An ordinary vaginal speculum may be used, shown in broken lines in FIG. 1, allowing separation of the vulva at the desired inclination.

Figure 3:
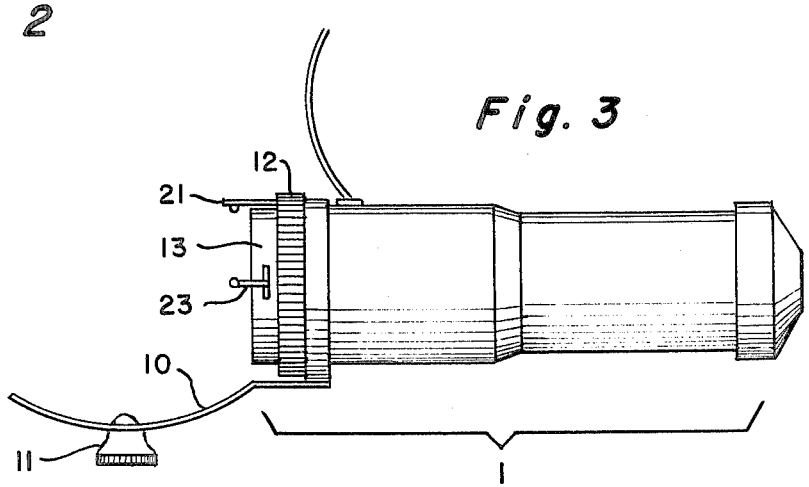
FIG. 3 is a side view of a guide-tube of the present invention.

In accordance with the invention, the instrument includes guide-tube means. As embodied herein, the guide-tube means includes guide-tube 1 (FIG. 3), which basically includes a circular tube approximately 3 cm in diameter (different diameters may be provided if desired), made of stainless steel, anodized aluminum, or any other material of adequate resistance permitting easy cleaning and disinfecting.

Figure 4:
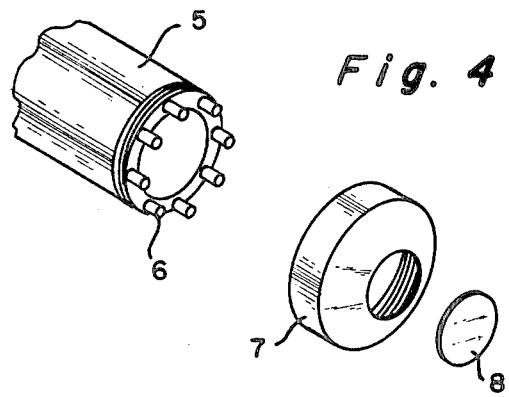
FIG. 4 is a perspective view showing the construction of the forward end of the guide tube.

In accordance with the invention, the forward end of the guide-tube means is provided with means for illumination. As embodied herein, the means for illumination includes a round metal base 5 (FIG. 4) screwed to the forward end of the tube 1 and a number of small electric spot-lights or lamps 6 mounted in the base. The number of lights may vary with the tube diameter, e.g. eight for the one 3 cm in diameter. Transparent material permitting direct visual examination covers an opening in the forward end of the tube. To this end, a threaded piece of transparent plastic 7 is screwed onto this end of the tube like a cap, to the center of which is joined a circular piece of glass 8 through which is obtained the microscopic focus.

Electric power is obtained from a small variable output transformer (3-24 volts, not shown).

Figure 2:
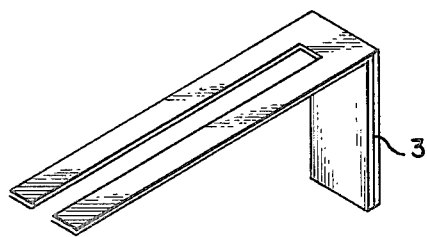
FIG. 2 is a perspective view of a fastener shown in FIG. 1.

In accordance with the invention, the guide-tube means includes means for attachment to the vaginal speculum. As embodied herein, for the attachment means, near the end opposite the cap 7, the guide-tube 1 is provided with a metal shoulder supporting a slightly curved concave dish or plate 10, adapted to be fastened to the vaginal speculum, that permits the guide-tube to be locked into the desired angle of inclination with respect to the vaginal speculum by means of a screw and nut 11. Once the speculum is introduced into the vagina, fastener 3 (FIG. 2) is used to fasten dish 10 to the guide-tube.

In accordance with the invention, the guide-tube means includes graduated focusing means to vary the length of the guide-tube means and thereby facilitate precise focusing of the microscope means. As embodied herein, the focusing means includes a knurled metal ring 12 provided with a screw-thread fine control. When turned clock-wise it will move forward ring 13 (FIG. 3), which slides over small fixed pivots. When turned in the other direction, it moves ring 13 in a rearward direction permitting the length of the tube to be varied within the approximate range of 4 millimeters, facilitating thereby the precise focusing of the microscope with the particular objectives.

Figure 5:
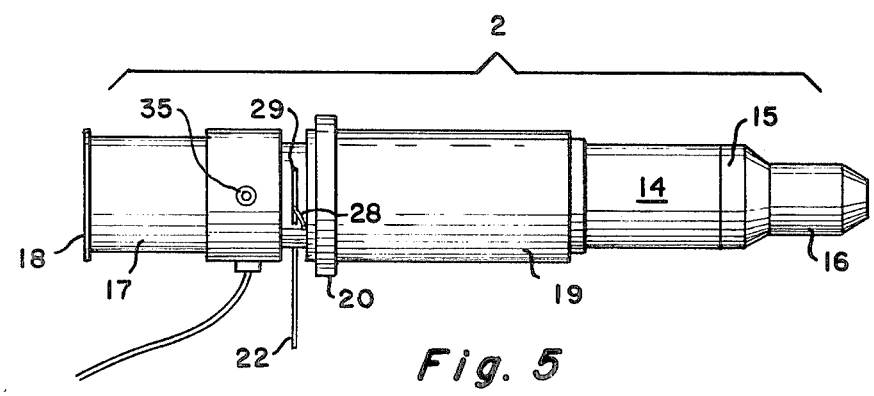
FIG. 5 is a side view of the actual microscope part of the present invention.

In accordance with the invention, the instrument includes microscope means, which, as embodied herein, is a microscope 2 (FIG. 5), which makes use of quality objectives and oculars for microscopes. It consists of a tube 14 of stainless steel (or other suitable metal) approximately 2 cm in diameter provided at its forward end with a screw thread 15 which keeps the objective 16 centered. It is provided at its rearward end with a hollow piece 17 that permits adjustment of ocular 18.

In accordance with the invention, the microscope means includes means rotatably positioned within the guide-tube means to rotate the microscope means about the axis of the guide-tube means, and means positioned eccentrically inside the rotatably positioned means, whereby upon rotation of the rotatably positioned means the microscope means rotates and changes microscope fields while the guide-tube remains stationary. For example, as embodied herein, tube 14 is the eccentrically positioned means and is placed slightly eccentrically inside the rotatably positioned means, tubular piece 19, so that the tube 14 rotates therein with slight friction. Piece 19 fits exactly in the guide-tube 1. Upon rotating graduated collar-plate 20, the microscope, without losing its focus, will rotate so as to permit examination of up to 30 distinct microscopic fields without moving the guide-tube. The graduations of the rotary piece are separated by 12° from one another, each held by a small catch 21 (FIG. 3) fastened to the rear ring of the guide-tube. The graduated collar permits indexing of piece 19 relative to the guide-tube.

This system offers the advantage of easily locating an interesting microscopic field previously examined.

In order to avoid microscopic motion with respect to its own axis, use is made of the small pin 22.

In accordance with the invention, the guide-tube means includes fine-adjustment clamp means. As embodied herein, the fine-adjustment clamp means are illustrated by clamps 23. The small fine-adjustment clamps 23 for fine control, one on each side, lock the microscope to the guide-tube without hampering its operation while preventing accidental movements.

Figure 6:
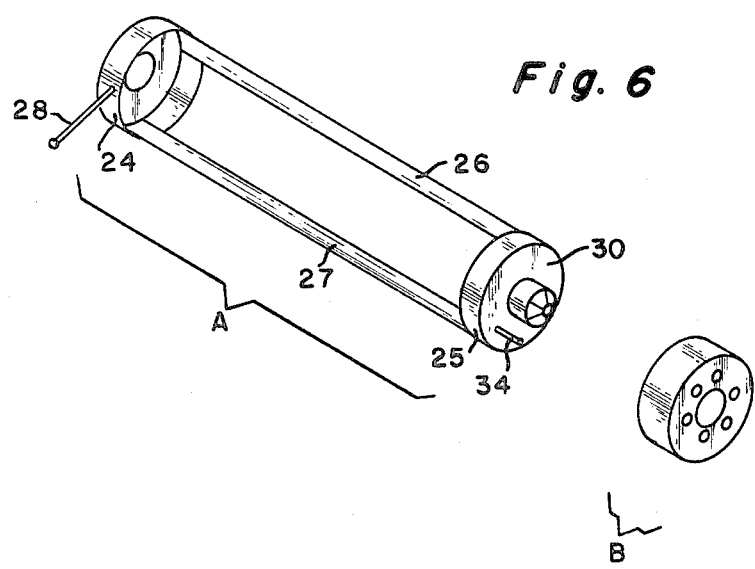
FIG. 6 is a perspective view showing the construction of the illuminating systems of the actual microscope part.
Figure 7:
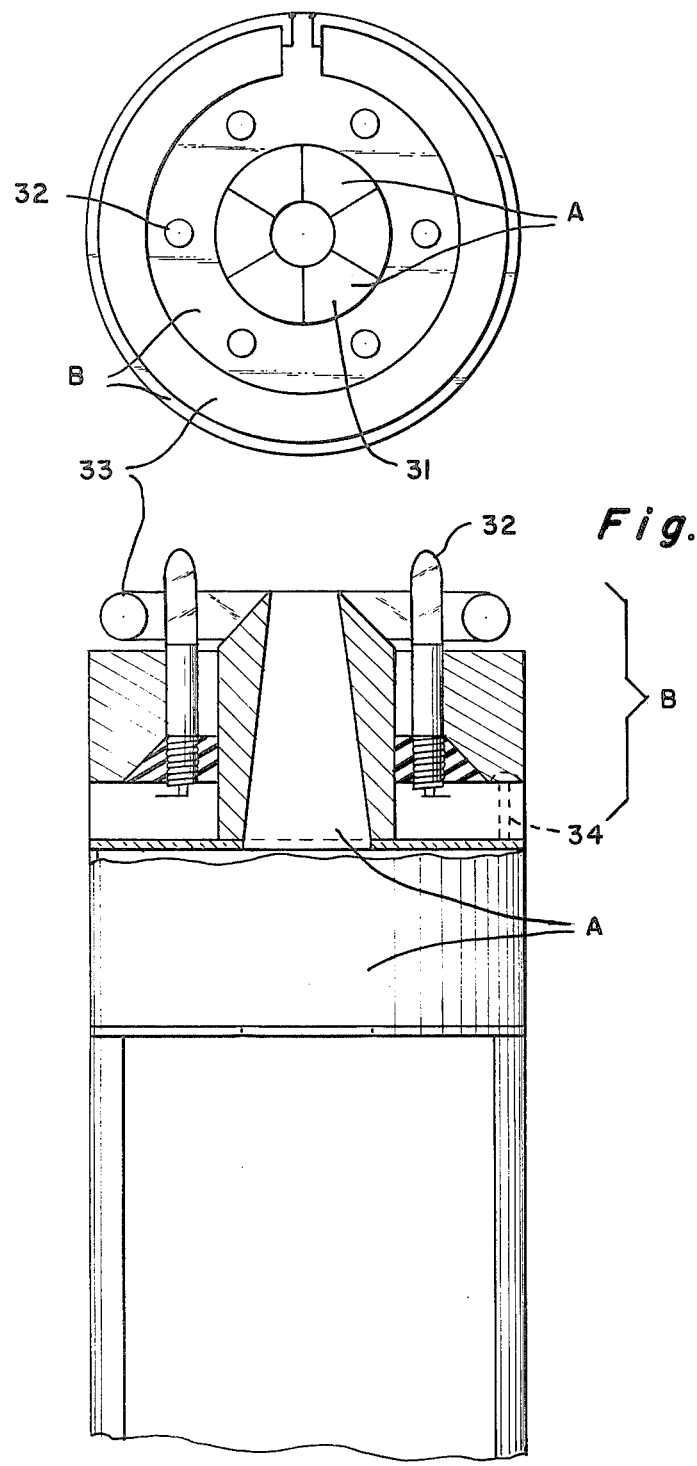
FIG. 7 is an exploded top plan view and an exploded partial sectional view of the illuminating systems of the actual microscope part.

In accordance with the invention, the microscope means includes first and second illumination means, which, as embodied herein, comprise one illumination system including a plurality of tiny electric lights or lamps and an annular illumination system including electronically caused flashes, both being mounted in pieces A and B and which are shown in approximately actual size in FIG. 6 of the drawings and which are magnified (approximately five times their actual size) in FIG. 7 of the drawings. They are shown assembled in FIG. 7.

Piece A (see FIG. 6) consists of a thin brass tube, cut open lengthwise, and two circular rings 24 and 25, which are interconnected only by two laminations 26 and 27 of the tube proper.

Screwed to the rear ring 24 is a small lever 28 projecting through a groove of the microscope tube 29. This groove extends through 30° of the tube circumference. Moving the lever causes rotation of piece A inside the microscope tube.

In accordance with the invention, the microscope means includes light condensor means. As embodied herein, the light condensor means comprises a front ring 25 locked by means of a circular plate 30 of insulating material. At the center of plate 30 is mounted a piece 31 of stainless steel which in turn is perforated at its center and includes six sides inclined at approximately 45° that act as small mirrors reflecting the light from the six tiny lamps of piece B in the forward direction through the lenses (elements) of the objective and as a condensor to illuminate the microscopic field.

The description and the operation of these systems will be continued below and for better comprehension, reference should be made to FIG. 7.

The two unassembled pieces A and B are clearly seen in the top plan view of FIG. 7. The view is along the axis of the microscope, away from the objective. The central part, piece 31, of piece A, is shown with its central aperture and the six reflecting sides mentioned above.

The components of piece B, namely the set of six tiny electric lamps 32 and around these a ring 33 of electronic flashes, are shown around piece 31.

When the small lever 28 of piece A is at the extreme upper position or stop of groove 29, the tiny lamps will remain aligned with the reflecting surfaces. When the small lever moves down to the lower end or stop of the groove, piece 31 will rotate by 30°. At the moment the reflecting sides of piece 31 are directed towards the space between each lamp, they will align exactly with the flashing light from the circular light source 33.

Metallic lever 34 of piece A is provided with the corresponding electrical contacts. When lever 28 is located in the upper part of groove 29, contact is established between the lamps and a small, variable output transformer (3 to 18 volts, not shown) by means of lever 34, whereby the lamps are activated and careful examination of each microscopic field is made possible.

If at that time a photograph is desired by means of a suitably coupled photographic camera, lever 28 merely need be lowered to its bottom stop. At precisely the 30° position, the electronic flash is activated and will instantaneously discharge. The contact is established by the same lever 34 of piece A.

When in the intermediate position, lever 28 disconnects lever 34 from both electrical circuits so that neither illumination system is activated to provide pauses eliminating overheating of the tiny lamps and thereby achieving maximum life.

The electronic flashing ring is connected to a small power connector 35, on piece 17, for the cable of the photographic camera. Another connector is located on the opposite side of the same piece 17 to hook up to the energy source of the "electronic flash."

The illuminating system, which is very simple, allows careful examination of each microscopic field at any magnification, and by means of a single movement of lever 28 an instantaneous photograph may be taken as often as desired.

Since the microscope may be easily inserted and withdrawn without moving the guide-tube, as many as 30 microscopic fields may be examined at variable magnifications, changing the objectives and the oculars whenever desired.

Some of the possible distinct magnifications are:

| Objective | × | Ocular | = | Magnification |
|---|---|---|---|---|
| 5× | | 5× | | 25× |
| 5× | | 10× | | 50× |
| 5× | | 15× | | 75× |
| 10× | | 5× | | 50× |
| 10× | | 10× | | 100× |
| 10× | | 15× | | 150× |
| 20× | | 5× | | 100× |
| 20× | | 10× | | 200× |
| 20× | | 15× | | 300× |
| 40× | | 5× | | 200× |
| 40× | | 10× | | 400× |
| 40× | | 15× | | 600× |
| 60× | | 5× | | 300× |
| 60× | | 10× | | 600× |
| 60× | | 15× | | 900× |

The microscope may be designed to be binocular or triocular with a factory assembled photographic camera.

What is claimed is:

1. An instrument for microscopic examination through the vagina comprising: guide-tube means including means for attaching said guide-tube within a speculum and microscope means adjustably positioned inside said guide-tube means.

2. The instrument of claim 1, wherein the forward end of said guide-tube means is provided with means for illumination and an opening covered with transparent material permitting direct visual examination therethrough.

3. The instrument of claim 2, wherein said means for illumination comprises a plurality of lamps.

4. The instrument of claim 1, wherein said guide-tube means includes graduated focusing means to vary the length of said guide-tube means and thereby facilitate precise focusing of said microscope means.

5. The instrument of claim 1, wherein said microscope means also includes interchangeable objectives and oculars, whereby examination at variable magnifications is possible.

6. An instrument for microscopic examination through the vagina comprising:
   (1) guide-tube means including means for attaching said guide-tube within a speculum; and
   (2) microscope means adjustably positioned inside said guide-tube means, said microscope means including means rotatably positioned within said guide-tube means to rotate said microscope means about the axis of said guide-tube means, and means positioned eccentrically inside said rotatably positioned means, whereby upon rotation of said rotatably positioned means said microscope means rotates and changes microscopic fields while said guide-tube means remains stationary.

7. The instrument of claim 6 wherein said rotatably positioned means includes a graduated collar permitting indexing of said rotatably positioned means relative to said guide-tube means.

8. An instrument for microscopic examination through the vagina comprising:
   (1) guide-tube means including means for attaching said guide-tube within a speculum, said means for attaching including a concave plate means for attachment to said speculum and for permitting adjustment of the angle of inclination of said guide-tube means relative to said speculum; and
   (2) microscope means adjustably positioned inside said guide-tube means.

9. An instrument for microscopic examination through the vagina comprising:
   (1) guide-tube means including means for attaching said guide-tube within a speculum; and
   (2) microscope means adjustably positioned inside said guide-tube means, said microscope means including first and second illumination means, said first illumination means comprising a plurality of lamps, and said second illumination means comprising an electronic flashing light source.

10. The instrument of claim 9, wherein said flashing light source is annular and said microscope means further includes a light condensor means surrounded by said first and second illumination means comprising a plurality of inclined mirrors that reflect light toward the elements of an objective.

11. The instrument of claim 10, wherein said microscope means further includes a tube positioned inside said microscope means and rotatable therein between two stops, said first and second illumination means being mounted on said tube, and wherein the first illumination means is activated at one of said stops while the second illumination means is not activated at said one of said stops, the second illumination means is activated at the other of said stops, while the first illumination means is not activated at said other of said stops, proper reflection of light is provided through said light condensor means whenever said tube is positioned at either of said two stops because of alignment of said illumination means when activated and said condensor means, and neither of said illumination means is activated when said tube is positioned intermediate said two stops.

12. An instrument for microscopic examination through the vagina comprising:
   (1) guide-tube means including means for attaching said guide-tube within a speculum, said guide-tube means including fine-adjustment clamp means to fasten a microscope means to said guide-tube means and prevent accidental movements while permitting movement of parts within said microscope means and rotation of said microscope means within said guide-tube means; and
   (2) said microscope means, said microscope means being adjustably positioned inside said guide-tube means.

13. An instrument for microscopic examination through the vagina comprising:
   (1) guide-tube means comprising:
      (a) means for attaching said guide-tube within a speculum including a concave plate means for attachment to said speculum and for permitting adjustment of the angle of inclination of said guide means relative to said speculum;
      (b) a plurality of lamps and an opening covered with transparent material on the forward end of said guide-tube means permitting direct visual examination therethrough;
      (c) graduated focusing means to vary the length of said guide-tube means;
   (2) microscope means adjustably positioned inside said guide-tube means including:
      (a) means rotatably positioned within said guide-tube means to rotate said microscope means about the axis of said guide-tube means;

(b) a graduated collar on said rotatably positioned means permitting indexing of said rotatably positioned means relative to said guide-tube means;

(c) means positioned eccentrically inside said rotatably positioned means, whereby upon rotation of said rotatably positioned means said microscope means rotates and changes microscopic fields while said guide-tube means remains stationary;

(d) first and second illumination means, said first illumination means comprising a plurality of lamps and said second illumination means comprising an annular flashing light source;

(e) light condensor means surrounded by said first and second illumination means said light condensor means comprising a plurality of inclined mirrors that reflect light toward the elements of an objective;

(f) a tube on which are mounted said first and second illumination means positioned inside said microscope means and rotable therein between two stops, the first illumination means being activated at one of said stops while the second illumination means is not activated at said one of said stops, the second illumination means being activated at the other of said stops while the first illumination means is not activated at said other of said stops, proper reflection of light being provided through said light condensor means whenever said tube is positioned at either of said two stops, because of alignment of said illumination means when activated and said condensor means, and neither of said illumination means being activated when said tube is positioned intermediate said two stops;

(3) fine-adjustment clamp means to fasten said microscope means to said guide-tube means and prevent accidental movements while permitting movement of parts within said microscope means and rotation of said microscope means within said guide means; and (4) interchangeable objectives and oculars for said microscope means, whereby examination at variable magnifications is possible.

14. An instrument for microscopic examination through the vagina comprising:

(1) guide-tube means including means for attaching said guide-tube within a speculum, the forward end of said guide-tube means being provided with means for illumination and an opening covered with transparent material permitting direct visual examination therethrough; and (2) microscope means adjustably positioned inside said guide-tube means, said microscope means including first illumination means comprising a plurality of lamps at the forward end of said microscope means.

15. The instrument of claim 14, wherein said microscope means further includes a light condensor means surrounded by said plurality of lamps at the forward end of said microscope means and surrounding the optical axis of said microscope means, said light condensor means comprising a plurality of inclined mirrors that reflect light toward the elements of an objective.

* * * * *